US00PP30494P2

(12) United States Plant Patent
Elst

(10) Patent No.: US PP30,494 P2
(45) Date of Patent: May 14, 2019

(54) ***CARYOPTERIS* PLANT NAMED 'ELST01'**

(50) Latin Name: *Caryopteris clandonensis*
Varietal Denomination: Elst01

(71) Applicant: Fransiscus Johannes Christiaan Elst, Wernhout (NL)

(72) Inventor: Fransiscus Johannes Christiaan Elst, Wernhout (NL)

( * ) Notice: Subject to any disclaimer, the term of this patent is extended or adjusted under 35 U.S.C. 154(b) by 0 days.

(21) Appl. No.: 15/731,487

(22) Filed: Jun. 12, 2017

(51) Int. Cl.
*A01H 5/02* (2018.01)

(52) U.S. Cl.
USPC ..... Plt./226
CPC ..... *A01H 5/02* (2013.01)

(58) Field of Classification Search
USPC ..... Plt./226
See application file for complete search history.

(56) References Cited

PUBLICATIONS

"Peter van Rijssen (Plantipp) kijkt vooruit: eenderde minder noviteiten op de markt," Boom in Business, downloaded from edepot.wur.nl/305368, pp. 34-37, published 2014.*

* cited by examiner

*Primary Examiner* — Anne Marie Grunberg
(74) *Attorney, Agent, or Firm* — Penny J. Aguirre

(57) ABSTRACT

A new cultivar of *Caryopteris* plant, 'Elst01', that is characterized by its long flowering stems with inflorescences comprised of large deep blue flowers, its long blooming period, its grey-green foliage, its short plant height, and its broadly upright plant habit.

2 Drawing Sheets

Botanical classification: *Caryopteris clandonensis.*
Cultivar designation: 'Elst01'.

BACKGROUND OF THE INVENTION

The present invention relates to a new and distinct cultivar of *Caryopteris, clandonensis* and will be referred to hereafter by its cultivar name, 'Elst01'. 'Elst01' represents a new herbaceous perennial grown for landscape use.

The new cultivar originated as a chance seedling growing in a production field of *Caryopteris clandonensis* 'First Choice' (U.S. Plant Pat. No. 11,958) at a nursery in Wernhout, The Netherlands in summer of 2011. 'First Choice' is therefore presumed to be the female parent and the male parent is unknown.

Asexual propagation of the new cultivar was first accomplished by stem cuttings by the Inventor in summer of 2012 in Boskoop, The Netherlands. Asexual propagation by cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Elst01' as a unique cultivar of *Caryopteris.*

1. 'Elst01' exhibits long flowering stems with inflorescences comprised of large deep blue flowers.
2. 'Elst01' exhibits a long blooming period.
3. 'Elst01' exhibits grey-green foliage.
4. 'Elst01' exhibits a short plant height.
5. 'Elst01' exhibits a broadly upright plant habit.

The probable female parent of 'Elst01', 'First Choice', differs from 'Elst01' in having foliage that is deep green in color, slightly lighter blue flowers, and a habit that is more mounding. 'Elst01' can also be compared to the *Caryopteris clandonensis* cultivar 'Inoveris' (U.S. Plant Pat. No. 17,837) and 'Elst33' (not patented). 'Inoveris' differs from 'Elst01' in having foliage that is greener in color, a more compact (shorter internodes) and broader plant habit, and smaller flowers. 'Elst33' is similar to 'Elst01' in having large blue flowers but differs from 'Elst01' in having much shorter flowering branches.

BRIEF DESCRIPTION OF THE DRAWINGS

The accompanying colored photographs illustrate the overall appearance and distinct characteristics of the new *Caryopteris*. The photographs were taken of an 18 month-old plant as grown outdoors in a 15-cm container in Wernhout, The Netherlands.

The photograph in FIG. 1 provides a side view of 'Elst01' in bloom.

Figure 1:
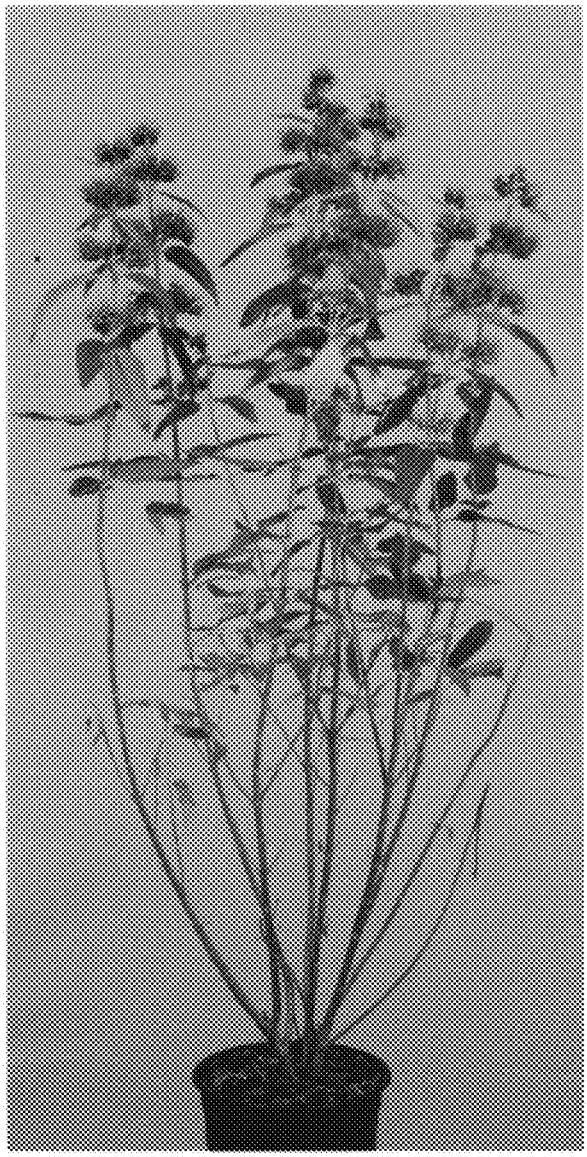
Figure 2:
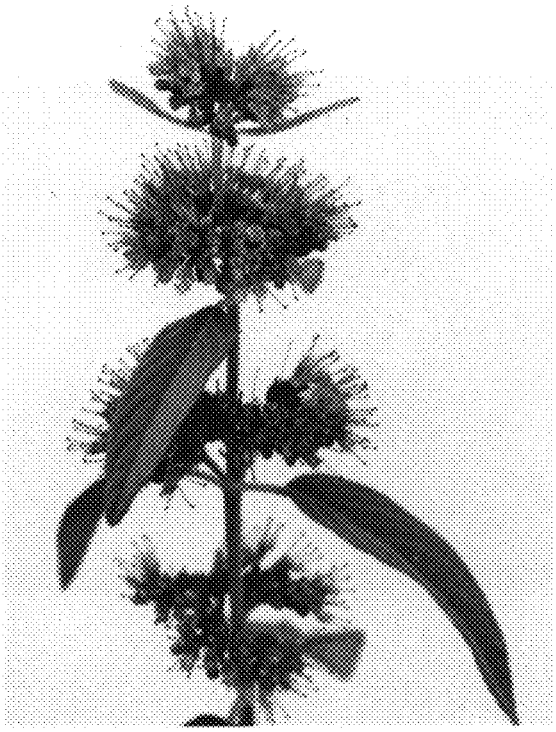

The photograph in FIG. 2 provides a close-up view of the inflorescences of 'Elst01'.

Figure 3:
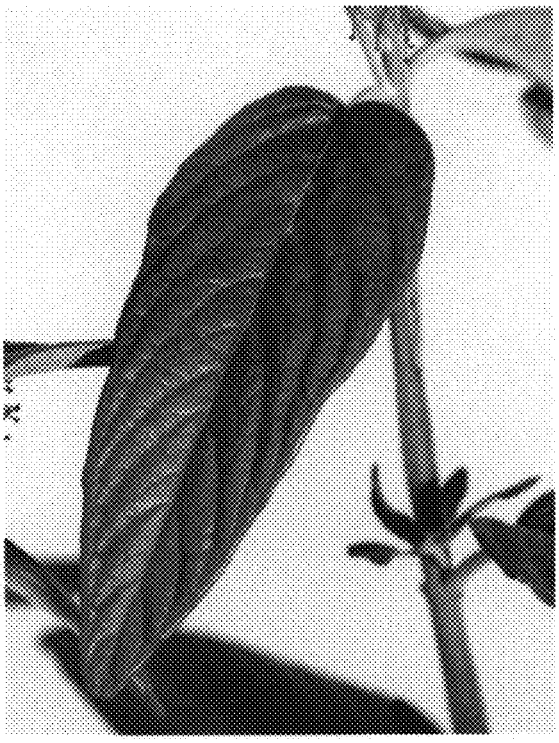

The photograph in FIG. 3 provides a close-up view of the foliage of 'Elst01'.

The colors in the photographs may differ slightly from the color values cited in the detailed botanical description, which accurately describe the colors of the new *Caryopteris.*

DETAILED BOTANICAL DESCRIPTION

The following is a detailed description of the new cultivar as observed for plants 18-months in age as grown 15-cm containers in Wernhout, The Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—Mid summer to early fall in The Netherlands.

*Plant type*.—Sub-shrub treated as a perennial.

*Plant habit*.—Broadly upright.

*Height and spread*.—Average of 83.7 cm in height, 45 cm in diameter as an 18 month-old plant.

*Hardiness*.—Hardy at least in U.S.D.A. Zones 5 to 8.

*Diseases*.—No susceptibility or resistance to diseases has been observed.

*Growth rate*.—Moderate to highly vigorous.

*Propagation*.—Stem cuttings.

*Root description*.—Fibrous, well-branched.

*Root development*.—Root initiate in about 8 days 72-cell liner and fully root in a liner as a young plants in about 6 weeks.

Stem description:

*Shape*.—Round.

*Stem quantity*.—Average of 27 stems.

*Stem color*.—Younger stems; N144A, older stems; 199A, striped with 199C to 199D.

*Stem size*.—Average of 4 mm in diameter, 44.8 cm in length.

*Stem surface*.—Matte, moderately covered with very short woolly pubescence, average of 0.1 mm in length and 157A in color.

*Stem aspect*.—Primarily upright.

*Branching habit*.—Moderately, freely branching.

*Stem fragrance*.—Pleasantly fragrant when touched.

*Stem strength*.—Moderately strong.

*Internode length*.—4.3 cm.

Foliage description:

*Leaf division*.—Simple.

*Leaf arrangement*.—Opposite.

*Leaf shape*.—Narrow ovate.

*Leaf size*.—An average of 7.2 cm in length and 2.9 cm in width.

*Leaf number*.—Average of 22.

*Leaf base*.—Round.

*Leaf apex*.—Acute.

*Leaf margin*.—Entire, coarsely undulate.

*Leaf venation*.—Pinnate, upper side 148B in color, lower side 145B in color.

*Leaf surface*.—Upper side is moderately glossy and slightly rugose, lower side is matte, both surfaces are densely covered with very short woolly pubescence an average of 0.1 mm in length and 157A in color.

*Leaf color*.—Young upper surface; 138B, young lower surface; 194B, mature upper surface; 137B, mature lower surface; 194A.

*Leaf attachment*.—Petiolate.

*Leaf petiole*.—Average of 1 cm in length, 2 mm in width, 145C in color, surface is glabrous.

*Leaf fragrance*.—Pleasantly fragrant when touched.

Flower description:

*Inflorescence type*.—Terminal and axillary dichasial cymes.

*Lastingness of inflorescence*.—Individual flowers last an average of 12 days, inflorescences lasts for about 5 weeks.

*Inflorescence size*.—Average of 3.8 cm in height and 5.3 cm in width.

*Inflorescence quantity*.—An average of 12 per stem.

*Flower type*.—Upright to outward, self-cleaning.

*Flower number*.—Average of 500 flowers per lateral stem, 6,000 flowers per plant.

*Flower fragrance*.—Faint.

*Flower buds*.—Obovate in shape, about 6 mm in length and 2.5 mm in diameter, mature bud; 93C in color, young bud; 147B, tinged 93B to 93C in color.

*Flower size*.—About 1.6 cm in depth and 5 mm in diameter.

*Peduncles*.—Average of 2.5 cm in length, 1 mm in diameter, angle varying between 0° and 35°, moderate in strength, 145C to 150C in color, matte surface.

*Pedicels*.—Average of 3 mm in length, 0.75 mm in diameter, held at an average angle of 25°, moderate in strength, 147C in color, matte surface.

*Calyx*.—Campanulate in shape, average of 3.5 mm in length and 2.5 mm in diameter.

*Sepals*.—5, campanulate, elliptic in shape, lower 42.5% of base is fused, both surfaces matte, entire margin, acute apex, 3.5 mm in length, 1.5 mm in width, immature and mature upper surface; 137C, immature and mature lower surface 147B, tinged with 93B to 93C.

*Petals*.—5, rotate with lower 75% fused into an irregular campanulate shape, lower lobe; considerably larger than upper 4 lobes, lower lobe; average of 1.3 cm in length and 4 mm in width, spathulate in shape, obtuse apex, laciniate margin, upper lobes; average of 8 mm in length and 2 mm in width, obovate in shape, obtuse apex, entire margin, both surfaces of all lobes matte and glabrous, color; when opening and fully open upper (inner) surface 91A, color when opening and fully open lower (outer) surface 93C, both surfaces of all lobes fade to 94B.

Reproductive organs:

*Gynoecium*.—Pistil; 1, 1.1 cm in length, style; and average of 1.05 cm in length and N88D, fading to NN155D in color, glabrous surface, stigma; decurrent, N87B in color, glabrous surface, ovary; 1 mm in diameter, N144B in color, glabrous surface.

*Androecium*.—Stamens; 4, filament; average of 1 cm in length, N88C in color, glabrous surface, anthers; dorsifixed and short-oblong in shape, average of 0.75 mm in length, N200A in color, glabrous surface, pollen is moderate in quantity and 16B to 16B in color.

*Fruit*.—Fruit and seed production has not been observed to date.

It is claimed:

1. A new and distinct cultivar of *Caryopteris* plant named 'Elst01' as herein illustrated and described.

* * * * *